United States Patent [19]

Klein

[11] 4,211,289
[45] Jul. 8, 1980

[54] SLEEVE WITH ARMBAND

[75] Inventor: Johann Klein, Cologne, Fed. Rep. of Germany

[73] Assignee: Bayer Aktiengesellschaft, Leverkusen, Fed. Rep. of Germany

[21] Appl. No.: 857,964

[22] Filed: Dec. 6, 1977

[51] Int. Cl.² ............................................. A61B 5/02
[52] U.S. Cl. ................................. 172/686; 128/327
[58] Field of Search ............. 128/2.05 C, 2.05 G, 128/327, 686, DIG. 20

[56] References Cited

U.S. PATENT DOCUMENTS

| | | | |
|---|---|---|---|
| 2,113,534 | 4/1938 | Brown | 128/327 |
| 3,603,304 | 9/1971 | Maier | 128/2.05 C |
| 3,606,880 | 9/1971 | Ogle | 128/2.05 C |
| 3,906,937 | 9/1975 | Aronson | 128/2.05 C |

*Primary Examiner*—George J. Marlo
*Attorney, Agent, or Firm*—Sprung, Felfe, Horn, Lynch & Kramer

[57] ABSTRACT

A device for use in measuring blood pressure comprises a cuff which is windable around the portion of a body and a clamp fastener for maintaining the cuff in the wound position during use. The fastener has a box shaped outer part and a box shaped inner part which is moveable therein perpendicular to the longitudinal access thereof and has slots in its end faces for receiving a pressure rod about which the cuff is looped. A sound pickup is disposed in the pressure chamber of the cuff and is connectable to a display instrument via an air tube.

9 Claims, 5 Drawing Figures

SLEEVE WITH ARMBAND

The invention relates to a sleeve for measuring blood pressure, which is wound and fixed around a part of the patient's body and has an inflatable pressure chamber.

Such sleeves are known per se and are formed either of a continuous rubber cloth, a textile web or a textile cloth lined with a separate rubber tube, with or without a sound pick-up. Earlier, simpler designs of such sleeves, are used as so-called pressure sleeves without means whereby it is simply possible to use a stethoscope for listening to the Korotkoff noise. Such sleeves may also be provided with a transmitter for transmitting signals via corresponding lines, for example pneumatic lines (cf. German Offenlegungsschrift No. 19 40 575).

In addition, sleeves are known which consist of a rubber bubble with a fabric covering, the fabric covering having a hook fastening or a burr closure.

The object of the invention is to provide a sleeve which is simpler to produce and simpler to fasten on the patient's arm.

According to the invention there is provided a sleeve for measuring blood pressure which is wound and fixed around a part of the patient's body and has an inflatable pressure chamber, the sleeve being of textile-coated rubber.

This has the advantage that a single smooth piece of material may be used as starting material and the sleeve can be produced by quickly sticking on the suitably folded layer. The need for separate sleeve bubble is avoided. It is also possible to make the required pressure chamber larger or smaller or with the optimum shape for the corresponding signal instrument rapidly and easily from a single starting piece of cut-out material. By cutting in an appropriate manner it is also easier than hitherto to provide openings for pipes to the sleeve bubble for filling the chamber with air. This also applies when a third pipe is provided as a connecting pipe from the sound pick-up to a sound transducer which is located in the instrument. In addition, the layer of textile is preferably part elastic or rubber elastic.

Although it is known simply to use rubberised fabric for other purposes, for example in inflatable boats and wet suits, the invention relates to a sleeve or an arm band in which the textile-coated rubber layer has a quite specific shape as a cut-out piece even in the starting condition and simply differs from rubberised fabric in this respect.

In an embodiment of the invention an L-shaped piece of the textile-coated rubber layer is used as the cut-out piece. Adhesive edges are advantageously so arranged in such a way that only a part of the band forms a pressure chamber, in particular in such a way that one longitudinal adhesive edge and several facial adhesive edges and in addition one longitudinal adhesive edge only extends over part of the length. This length is determined according to the invention by the length of a L-tab so that the compressed air chamber may be made larger or smaller by the shape of this tab by simply adapting the cut-out piece.

In an embodiment of the invention the sleeve or the sleeve band is connected with a clamp. This clamp serves as a rapid action fastener and is characterised according to the invention in that it consists of a box-shaped outer part and another box-shaped inner part which moves perpendicularly to the longitudinal axis therein, a side wall of the outer part is cut out and a pressure rod is arranged to pass through slots in the faces of the inner part parallel to the longitudinal axis, and the armband is fixed to a side face of the inner part and the pressure rod surrounds it in the form of a hairpin.

An embodiment of the invention is shown in the accompanying drawings, in which.

Figure 1:
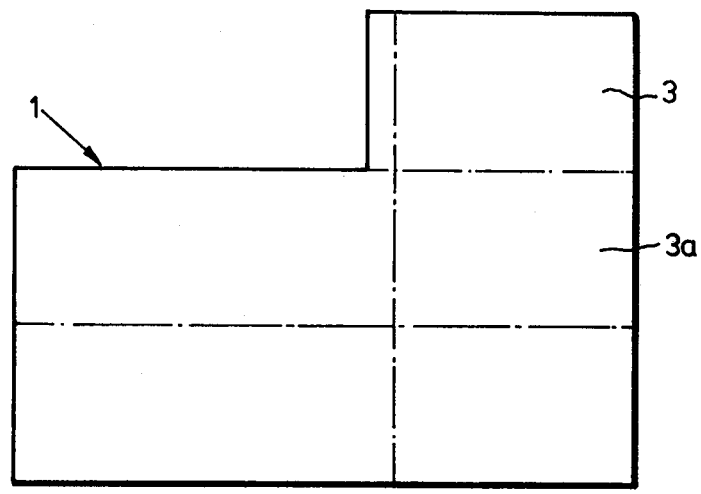
FIG. 1 is a plan view of a starting piece of material to the arm band before adhesion.
Figure 2:
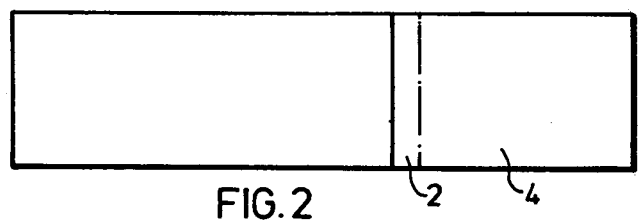
FIG. 2 is a plan view of the adhered sleeve piece, a chamber for compressed air being shown at the right hand side of this figure.

FIG. 1 shows a generally L-shaped cut-out piece 1 which is to form the arm band. The dot-dash lines indicate the position of subsequent fold lines used to produce the arm band shown in FIG. 2. In the simplest case, the front faces are stuck together and tabs 3 of the L-shaped piece as well as edges 3a are stuck to the other open sides by means of an adhesive edge 2 so that a compressed air chamber 4 is formed. Rubberised linen may be used as the material.

Figure 3:
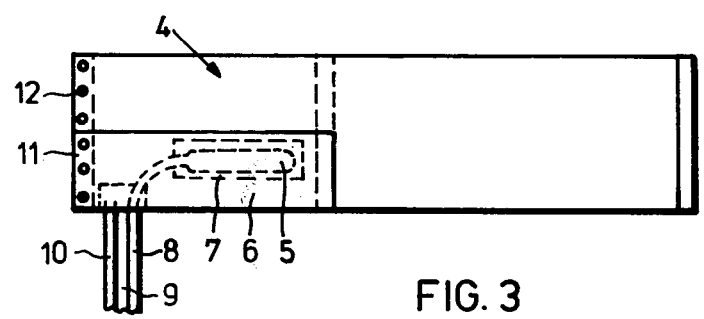
FIG. 3 shows an adhered sleeve with a chamber for compressed air in the left half and an acoustic chamber located within the compressed air chamber.

FIG. 3 shows a sound pick-up 5 closed or reinforced by a cover 6. The sound pick-up is fixed in advance to a backing 7. Air tubes 8 or 9 and 10 serve to connect the sound pick-up to an instrument (cf. for example German Offenlegungsschrift No. 1 940 575). The tubes 9 and 10 are either connected to a compressed air pump or, in the case of a simple pressure sleeve, to a doctor's rubber bellows.

Figure 4:
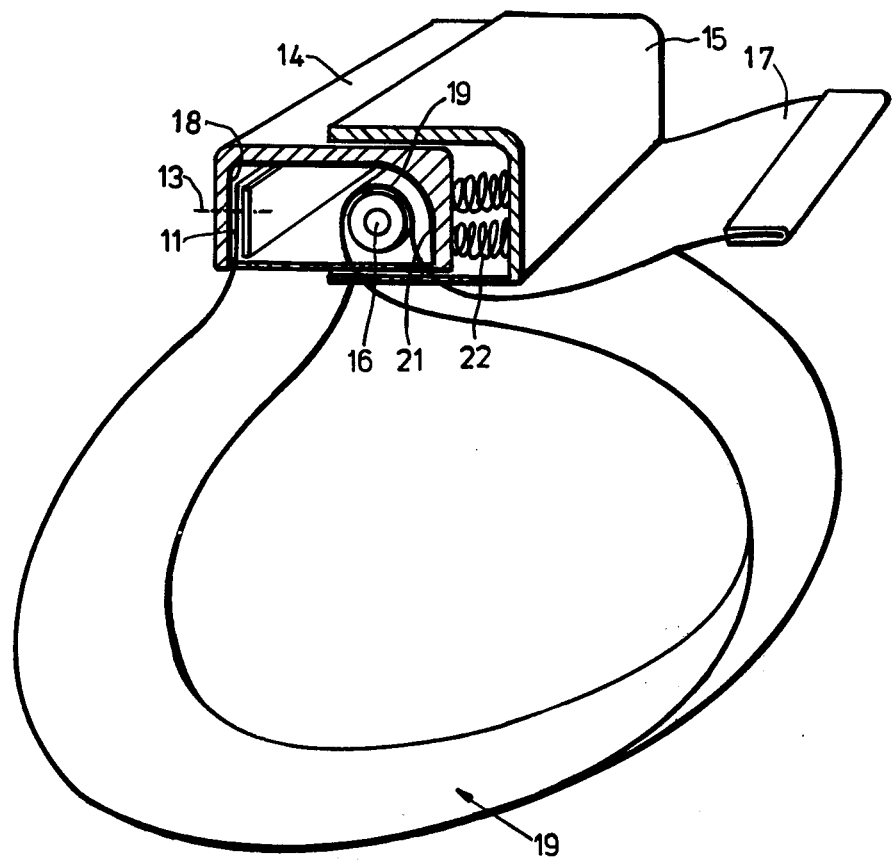
FIG. 4 is a perspective view of an embodiment of a rapid-action fastener for use in the invention.
Figure 5:
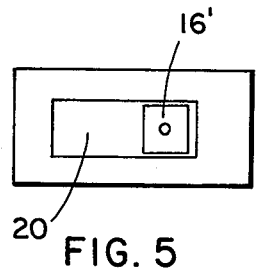
FIG. 5 is a detail of an alternate embodiment of FIG. 4.

A novel rapid-action fastener is used for fixing the sleeve to the patient's arm. As shown in FIG. 4 this consists of a box-shaped outer part 15 and another box-shaped inner part 14. The inner part is movable within the outer part perpendicularly to the longitudinal axis. An end 11 of the armband is fixed to a side wall 18 of the inner part by means of locations 13 for screws. A pressure rod 16 having a circular cross-section but preferably of rectangular cross-section, as shown in FIG. 5 as 16' passing through the inner part is screwed to the faces of the outer part. As the pressure rod 16 is fixed to the outer part 15, the faces of the inner part 14 have to be provided with slots 20 or slits so that the movement of the inner part is not restricted by the pressure rod 16. The pressure rod 16 thus extends through the slots 20. The other end 17 of the armband is looped round the pressure rod 16 in the manner of a hairpin. The part running between the pressure rod 16 and the side wall 18 of the inner part 14 forms a loop. A relatively narrow gap remains between the pressure rod 16 and the other side wall 21 when the inner part is in its starting position. The end of the armband 17 is fed out through this gap. The side wall 21 is roughened or provided with ribs on the side opposite the armband. Compression springs 21 are arranged between the outer side of the side wall 21 and the opposite inner face of the outer part 15 so that the inner part 14 can only be inserted in to the outer part 14 against spring pressure. The inner part 14 is the furthest outside in the starting position. In this way, the armband is frictionally clamped between the pressure rod 16 and the side wall 21.

When applying the sleeve, the loop 19 is pushed over the upper arm of the patient. The inner part 14 and outer part 15 are then pressed together with one hand while the free end 17 is drawn out with the other hand until the loop 19 fits tightly on the patient's upper arm. If the rapid-action fastener is now released, the inner part 14 returns to its starting position owing to the pressure of the spring. The clamping action described above thus takes place so that the loop 19 is fixed in this position on the patient's arm. It is then possible to begin measuring the blood pressure. This rapid-action fastener has proved successful both with manual activation and with automatically operating instruments. Earlier designs of automatically operating instruments frequently gave rise to the problem of interference (crackling) being produced when the pressure chamber was inflated, thus falsifying the measured result. Such interference was either induced by the material or originated from the sleeve fastener which produced crackling noises itself when loaded. Surprisingly, it has now been found that the novel fastener in combination with the sleeve material according to the invention functions without inducing such interferences.

What we claim is:

1. A device for use in measuring blood pressure comprising: a cuff which is windable around a portion of a body and clamp fastening means for maintaining the cuff in the wound position during use comprising a box-shaped outer part having an open side wall parallel to the longitudinal axis of the outer part and a box-shaped inner part which is movable therein perpendicularly with respect to the longitudinal axis of the outer part and has slots in the end faces thereof perpendicular to the longitudinal axis of the outer part, a pressure rod fastened to two opposite sides of the outer part and arranged to pass through the slots in the end faces of the inner part to be parallel to the longitudinal axis of the outer part, and the cuff being fixed to a side face of the inner part parallel to the longitudinal axis of the outer part and looping the pressure rod in the manner of a hairpin.

2. A device according to claim 1, wherein the cuff comprises at least one inflatable pressure chamber and is composed of textile-coated rubber.

3. A device according to claim 1, wherein the textile coating is one of part elastic or rubber elastic.

4. A device according to claim 1, wherein the cuff is formed from a generally L-shaped piece of material.

5. A device according to claim 4 wherein the material has at least one adhesive edge applied transversely to the longitudinal axis of the cuff to form the at least one pressure chamber.

6. A device according to claim 5, wherein the pressure chamber with its at least one adhesive edge forms only a part of the cuff.

7. A device according to claim 1, further comprising a sound pick up in the pressure chamber.

8. A device according to claim 6, wherein the sound pick-up is placed under a cover.

9. A device according to claim 7, wherein the sound pick-up comprises an acoustic chamber connectable to a display instrument via an air tube.

* * * * *